United States Patent [19]

Toce

[11] Patent Number: 5,714,598
[45] Date of Patent: *Feb. 3, 1998

[54] SULFATED ACID AMIDES HAVING ANTICOAGULANT PROPERTIES

[75] Inventor: Joseph A. Toce, Webster Groves, Mo.

[73] Assignee: Reliable Biopharmaceutical Corporation, St. Louis, Mo.

[*] Notice: The term of this patent shall not extend beyond the expiration date of Pat. No. 5,589,588.

[21] Appl. No.: 538,628

[22] Filed: Oct. 4, 1995

Related U.S. Application Data

[63] Continuation of Ser. No. 40,112, Mar. 30, 1993, Pat. No. 5,589,588.

[51] Int. Cl.$^6$ .............................. A61K 31/735; C08B 37/00
[52] U.S. Cl. .............................. 536/53; 536/54; 536/55.1; 536/55.3; 536/124; 514/54
[58] Field of Search .............................. 536/53, 54, 55.1, 536/55.3, 124; 514/54

[56] References Cited

U.S. PATENT DOCUMENTS 5,008,247   4/1991   Meinetsberger .............................. 514/23

FOREIGN PATENT DOCUMENTS 0 312 086   4/1989   European Pat. Off. .
0 312 087   4/1989   European Pat. Off. .

OTHER PUBLICATIONS

Emmerling et al., *Carbo. Research*, 86:321–324, 1980.

*Primary Examiner*—Kathleen K. Fonda
*Attorney, Agent, or Firm*—Darby & Darby

[57] ABSTRACT

A sulfated acid amide having heparin-like properties of the formula:

$$(R_1)\text{---NH---R---NH---}(R_1)$$

where $R_1$ is a di-, tri- or tetra-saccharide acid selected from cellobiose, cellotriose, cellotetrose, maltose, maltotriose and maltotetrose or mixtures thereof, and R is an alkylene of from 3 to 12 carbons, and is optionally substituted with one or more hydroxyls.

6 Claims, 1 Drawing Sheet

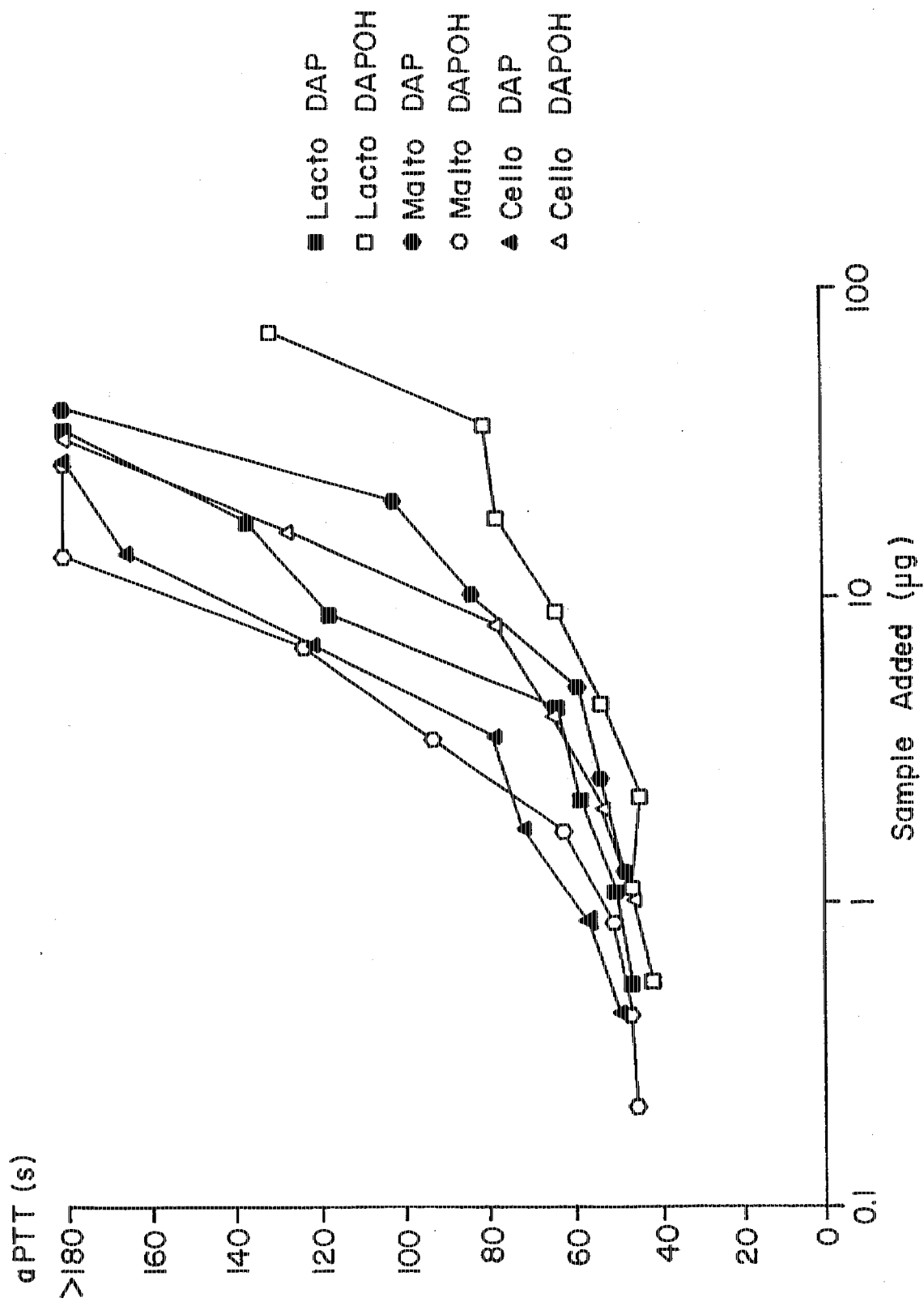

SULFATED ACID AMIDES HAVING ANTICOAGULANT PROPERTIES

This is a continuation of co-pending application Ser. No. 08/040,112 filed on Mar. 30, 1993, now U.S. Pat. No. 5,589,588.

FIELD OF THE INVENTION

The present invention relates to sulfated cellobionic acid amides and sulfated maltobionic acid amides having anticoagulant properties, and a method of preparing such amides.

BACKGROUND OF THE INVENTION

Heparin has been used as an effective antithrombotic drug for about fifty years. However, heparin has several side effects associated with its use, such as bleeding and heparin-induced thrombocytopenia. As a result, efforts have been made to develop better antithrombotic agents that do not exhibit such effects. It is further desirable to provide an antithrombic drug which can be administrated orally and is therefore stable in the patient's digestive system.

One approach has been to prepare low molecular weight compounds from heparin. U.S. Pat. No. 4,401,758 discloses oligosaccharides having no more than eight saccharidic moieties possessing anti-Xa activity. The above oligosaccharides are prepared by the depolymerization of heparinic material with nitrous acid. The oligosaccharides so produced are a mixture oligosaccharides, including those having six or fewer saccharides. U.S. Pat. No. 4,777,161 discloses a similar compound comprising a pentasaccharide prepared from alcoholic fractionation of heparinic material.

A second approach is the sulfation of polysaccharides. A sulfated pentasaccharide that binds to AT-III is disclosed by Sinay et al. "Total Synthesis of a Heparin Pentasaccharide Fragment having high Affinity for Antithrombin III," *Carbohydrate Research*, 132 (1984) C5–C9. A sulfated pentasaccharide prepared from D-glucose and D-glucosamine is disclosed by Choay et al, "Structure-Activity Relationship in Heparin: A Synthetic Pentasaccharide with high Affinity for Antithrombin III and Eliciting high Anti-Factor Xa Activity," *Biochemical and Biophysical Research Communications*, 116, No. 2, (1983) 492–499. Choay found that while the tetrasaccharide is ineffective in binding antithrombin III, the pentasaccharide is effective. C. R. Ricketts discloses dextran sulfate polysaccharides in "Dextran Sulfate-A Synthetic Analogue of Heparin," Biochem J, 51 (1952) 129, having heparin-like activity.

A third approach is to synthesize antithrombotic substances from lactobionic acid and a diamine. Klauser et al, "Biochemical Studies on Sulfated Lactobionic Acid Amides," *Seminars in Thrombosis and Hemostasis*, 17 (1991) supp. 1, 118, discloses sulfated lactobionic acid amides having antithrombic properties. The amides so prepared are single chemical entities without heterogeneity in composition or molecular weight, unlike heparin and its derivatives which are a mixture of compositions and molecular weights. Such a lactobionic compound may be attacked in the digestive system by lactase, when orally administered.

The above references fail to disclose the present sulfated cellobionic acid amides and sulfated maltobionic acid amides having anticoagulant properties, suitable for oral administration, and the method of preparing such amides.

SUMMARY OF THE INVENTION

The present invention relates to a sulfated acid amide having heparin-like properties comprising a compound of the formula:

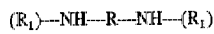

wherein $R_1$ is a sulfated di-, tri- or tetra-saccharide acid, or mixtures thereof, selected from the group consisting of cellobiose, cellotriose, cellotetrose, maltose, maltotriose and maltotetrose, and R is a hydrocarbon chain of from 3 to 12 carbons, and is optionally substituted with one or more hydroxyls.

The present invention further relates to a method for preparing the above sulfated acid amide comprising oxidizing a di-, tri- or tetra-saccharide or mixtures thereof selected from the group consisting of cellobiose, cellotriose, cellotetrose, maltose, maltotriose and maltotetrose by electrochemical oxidation, to form the acid, dehydrating the acid to form the lactone, condensing the above lactone with a diamine of the formula

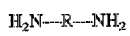

wherein R is a hydrocarbon chain of from 3 to 12 carbons, and is optionally substituted with one or more hydroxyls, to form an acid amide and sulfating the acid amide to form a sulfated acid amide having heparin-like properties.

DRAWING

The single FIGURE is a plot of weight of sample added versus clotting time.

DETAILED DESCRIPTION OF THE INVENTION

The present invention provides an antithrombic drug which can be administered orally and is therefore stable in the patient's digestive system. Compounds derived from lactose, which is readily broken down in saliva, may not be suitable for oral administration. Maltese, maltotriose and maltotetrose may be used, since the enzyme required to cleave maltose, i.e., maltase, may be present in low enough levels in the digestive system not to affect adversely the efficacy of the drug. The cellobiose, cellotriose and cellotetrose are not cleavable by mammalian digestive enzymes, and are therefore suitable starting materials. Maltose and cellobiose are the preferred starting disaccharides, since they are readily available compounds.

The sulfated acid amides of the present invention are prepared by first oxidizing the disaccharide using conventional oxidation methods as follows:

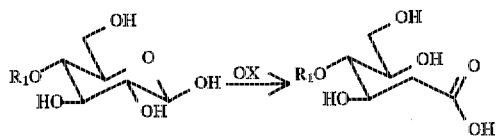

The preferred oxidation method is an electrochemical conversion process to form cellobionic or maltobionic acid.

The disaccharide can be dissolved in water and buffers, such as calcium carbonate, to maintain the pH between 4.5 and 7.0. Bromide salt, such as calcium bromide, sodium bromide or potassium bromide is added as the electrolyte used in the electrochemical conversion. The carbohydrate to bromide is present in the molar ratio in the range of 10 to 13. The preferred bromide salt is calcium bromide. The mixture of disaccharide, water, buffer and bromide salt can be placed in an electrolysis chamber. The chamber is cooled with a cooling loop to a temperature in the range of about 12° to 25° C., preferably in the range of about 17° to 20° C.

A potential, in the range of 4 to 8 volts, preferably about 6 volts, is applied to the chamber using electrodes, such as graphite electrodes. Below about 4 volts, the oxidation rate is extremely slow. The potential can applied for a sufficiently long period of time that the conversion to acid is essentially complete (>99%). During the oxidation reaction, base can be added to keep the pH between 4.5 and 7.0. After the reaction is complete, the pH can be adjusted in the range of about 1 to 4, and the residual ions removed by suitable means, such as ion exchange resins. The disaccharide acid can be recovered by spray drying.

The disaccharide acid can be converted to the lactone form by dehydration prior to condensation with the diamide as follows:

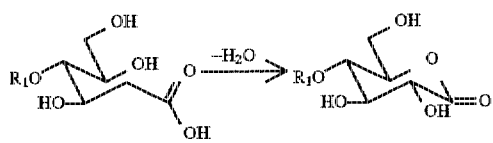

The lactone form can be prepared by refluxing the acid in an acidic alcohol solution such as a methoxyethanol/pentane/acetic acid solution. The acid form of the disaccharide can be condensed with a diamine, such as propanediamine, butanediamine, pentanediamine, or 1,3-diamino-2-hydroxypropane, as follows:

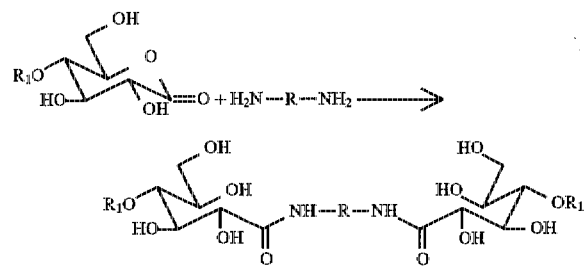

where R is a hydrocarbon chain of from 3 to 12 carbons. The bis-amide product can be purified from the starting materials by ion exchange chromatography. The product can be collected and dried using conventional methods.

The bis-amide can be sulfated using a complex, such as piperidine-N-sulfonic acid or sulfurtrioxide-pyridine. The sulfated bis-amide can be purified by ion exchange and analysed by HPLC and NMR. The level of sulfation can be determined by elemental analysis, and is typically greater than about 25 mole % of the available hydroxyls. The preferred level of sulfation is typically greater than about 50 mole %.

The anticoagulant activities of the above sulfated acid amides can be determined by standard in vitro methods used to monitor heparin therapy. The sulfated bis-amides can be tested for prolongation of the activated partial time and thrombin time (TT) of human plasma using commercial reagents.

The following examples are for illustrative purposes only and are not intended to limit the claims in any manner.

EXAMPLES

Example 1

Synthesis of Sulfated Bis-Maltobionic Acid Propylamide
Synthesis of the Disaccharide Maltose (1 kg, 2.92 moles) is dissolved into 3.8 l, deionized water with heating, in the range of about 40° C. to 60° C., or sufficient to dissolve the maltose. Calcium carbonate (381 g, 3.81 moles) and calcium bromide (51 g, 0.26 mole) are added with mixing. The solution is poured into an electrolysis chamber equipped with a cooling loop and cooled. Six volts DC are applied to opposite graphite electrodes. At 8 hour intervals, the potential is reversed. After 24 h, maltose (1 kg, 2.92 moles) is added and electrolysis is continued until essentially all of the maltose is converted to its acid form (as measured by HPLC), about 104 h total time. The solution is filtered to remove excess calcium carbonate and the pH of the filtrate is adjusted to 2.0 with sulfuric acid. The solution is cooled about 12 to 16 h to 8° C., and filtered to remove calcium sulfate. Calcium ions are removed by batch adsorption to Amberlite IRA 120 resin in the hydrogen form. The sulfate and bromide ions are removed by batch adsorption to Amberlite IRA 68 resin in the hydroxide form. The solution is spray dried with a Bowen 3 ft (1 m) flat bottom laboratory spray drier with a 2 fluid nozzle atomizer. The inlet temperature is kept at about 280° F. to 300° F. (138° C. to 149° C.) with all ports closed. The cellobionic acid is produced in the same manner from cellobiose.

Synthesis of the Bis-Amide

Maltobionic acid (10 g, 0.028 mole) is refluxed in 300 ml of methoxyethanol:pentane (2:1) and 0.2 ml of acetic acid in a Dean Stark apparatus purged under nitrogen atmosphere. The sugar acid is refluxed until it is essentially all converted to the lactone. The mixture is neutralized with 0.3 ml anhydrous pyridine. After the mixture is cooled, 1.1 ml (0.013 mole) of 1,3-diaminopropane is added over 1 h with mixing. Stirring is continued for 2 to 3 h to allow for precipitation of the desired product. The solids are collected and dried under vacuum.

Sulfation of Bis-amide

The bis-amide (0.3 g, 0.0004 mole) is suspended in 25 ml of dried dimethylsulfoxide (DMSO) and cooled. Sulfurtrioxide-pyridine complex (5×molar amount) is added at a rate of 1 g/15 min while keeping the suspension cool. The suspension is allowed to warm to room temperature while stirring overnight. The suspension is neutralized with sodium bicarbonate with mixing and diluted with an equal volume of deionized water. After filtration, the filtrate is charged onto an anion exchange resin. The column is washed with solutions of sodium chloride and the sulfated heparinoids are eluted with a high salt wash. The material is desalted by utrafiltration and vacuum dried. Elemental analysis indicates 19.75 weight % carbon and 14.77 weight % sulfur. The level of sulfonation is 48%.

Example 2

Synthesis of Sulfated Bis-Cellobionic Acid Propylamide

The same method as described in Example 1 is used to prepare sulfonated bis-cellobionic acid propylamine. Elemental analysis indicates 18.91 weight % carbon and 17.65 weight % of sulfur. The level of sulfation is 59%.

Example 3

Synthesis of Sulfated Bis-Maltobionic Acid Hydroxy-Propylamide

The same method as described in Example 1 is used to prepare sulfonated bis-maltobionic acid hydroxy-propylamine. Elemental analysis indicates 18.33 weight % carbon and 16.84 weight % sulfur. The level of sulfation is 55%.

Example 4

Synthesis of Sulfated Bis-Cellobionic Acid Hydroxy-Propylamide

The same method as described in Example 1 is used to prepare sulfonated bis-cellobionic acid hydroxypropylamine. Elemental analysis indicates 17.32 weight % carbon and 14.54 weight % sulfur. The level of sulfation is 50%.

Control 1

Synthesis of Sulfated Bis-Lactobionic Acid Propylamide

The same method as described in Example 1 is used to prepare sulfated bis-lactobionic acid propylamine. Elemental analysis indicates 18.97 weight % carbon and 15.73 weight % sulfur. The level of sulfation is 52%.

Control 2

Synthesis of Sulfated Bis-Lactobionic Acid Hydroxy-Propylamide

The same method as described in Example 1 is used to prepare sulfated bis-lactobionic acid hydroxy-propylamine. Elemental analysis indicates 18.37 weight % carbon and 17.27 weight % sulfur. The level of sulfation is 56%.

Examples 1 through 4, and controls 1 and 2 were evaluated for activated partial thromboplastin time (aPPT) according to the following procedure supplied by Sigma Chemical:

W. J. Williams et al, Hematology., 4th ed.,

McGraw Hill, 1990, p. 1766.

The FIGURE is a plot of the weight of sample added (ug) versus the clotting time (s) for Examples 1 through 4 and Controls 1 and 2. The samples differ in specific activity by about one (1) order of magnitude, with sulfated bis-maltobionic acid hydroxy-propylamide and sulfated bis-cellobionic acid propylamide having the highest activity, and sulfated bis-lactobionic acid hydroxy-propylamide being the least active.

Although the foregoing includes a description of the best mode contemplated for carrying out the invention, various modifications are contemplated.

As various modifications could be made in the compositions and methods herein described and illustrated without departing from the scope of the invention, it is intended that all matter contained in the foregoing description or shown in the accompanying drawing shall be interpreted as illustrative rather than limiting.

I claim:

1. A compound of the formula:

$$\left[ XO-CH_2-CH(OX)-CH(OR^1)-CH(OX)-CH(OX)-\underset{\|}{\overset{O}{C}}-NH-\right]_2 R$$

wherein R is a hydrocarbon chain of from 3 to 12 carbons substituted with one or more hydroxyl groups;

each $R^1$ is independently selected from the group consisting of wherein each m is independently from 0 to 2; and each X is independently selected from the group consisting of hydrogen or $-SO_3H$, where at least one X is $SO_3H$.

2. The compound of claim 1, wherein each $R^1$ is the same and m is 0.

3. The compound of claim 1, wherein R is an hydrocarbon chain having 3 to 5 carbon atoms and is substituted with one or more hydroxyl groups.

4. The compound of claim 2 wherein R is $$\underset{CH(CH_2)_2}{\overset{OH}{|}}.$$

5. A method for preparing a sulfated acid amide, which comprises:

forming an acid amide by condensing a member selected from the group consisting of cellobionic acid, cellotrionic acid, cellotetraonic acid, maltobionic acid, maltotrionic acid, maltotetraonic acid, and mixtures thereof with a diamine of the formula $$H_2N-R-NH_2$$

wherein R is a hydrocarbon chain of from 3 to 12 carbons and is substituted with one or more hydroxyl groups; and sulfating said acid amide to form a sulfated acid amide.

6. The method of claim 5 which comprises electrochemical oxidation of a member selected from the group consisting of cellobiose, cellotriose, cellotetraose, maltose, maltotriose, maltotetraose, and mixtures thereof.

* * * * *